(12) United States Patent
Otomo et al.

(10) Patent No.: US 8,053,193 B2
(45) Date of Patent: Nov. 8, 2011

(54) METHOD AND APPARATUS FOR JUDGING THE PRESENCE OR ABSENCE OF CANCER CELL

(75) Inventors: Yasuhiro Otomo, Kobe (JP); Kazuki Nakabayashi, Kobe (JP); Kayo Shoji, Kobe (JP); Hideki Takata, Kobe (JP)

(73) Assignee: Sysmex Corporation, Hyogo (JP)

( * ) Notice: Subject to any disclaimer, the term of this patent is extended or adjusted under 35 U.S.C. 154(b) by 181 days.

(21) Appl. No.: 12/175,805

(22) Filed: Jul. 18, 2008

(65) Prior Publication Data

US 2009/0081671 A1    Mar. 26, 2009

(30) Foreign Application Priority Data

Sep. 20, 2007 (JP) ................................ 2007-243989

(51) Int. Cl.
*C12Q 1/68* (2006.01)
*G01N 33/53* (2006.01)

(52) U.S. Cl. ........................................ 435/6.14; 435/7.1

(58) Field of Classification Search .................. None
See application file for complete search history.

(56) References Cited

U.S. PATENT DOCUMENTS

| 5,637,687 | A | 6/1997 | Wiggins |
|---|---|---|---|
| 2003/0124128 | A1 | 7/2003 | Lillie et al. |
| 2003/0143572 | A1 | 7/2003 | Lu et al. |
| 2005/0042138 | A1 | 2/2005 | Ueda et al. |
| 2005/0260646 | A1 * | 11/2005 | Baker et al. ............... 435/6 |
| 2006/0121515 | A1 | 6/2006 | Otomo et al. |
| 2007/0172857 | A1 | 7/2007 | Daito et al. |
| 2007/0264635 | A1 | 11/2007 | Suzuki et al. |

FOREIGN PATENT DOCUMENTS

| EP | 1508809 A1 | 2/2005 |
|---|---|---|
| EP | 1813682 A1 | 8/2007 |
| WO | 02/103320 A2 | 12/2002 |
| WO | 03/017038 A2 | 2/2003 |
| WO | 2004/024957 A2 | 3/2004 |

OTHER PUBLICATIONS

Manabu Yamamoto et al., "Peritoneal lavage CEA/CA125 is a prognostic factor for gastric cancer patients", J. Cancer Res. Clin. Oncol., 2007, 133:471-476.
Yih-Huei Uen et al., "Clinical significance of MUC1 and c-Met RT-PCR detection of circulating tumor cells in patients with gastric carcinoma", Clinica Chimica Acta, 2006, 367: 55-61.
G. Gargano et al., "Detection and quantification of mammaglobin in the blood of breast cancer patients: can it be useful as a potential clinical marker? Preliminary results of a GOIM (Gruppo Oncologico dell'Italia Meridionale) prospective study", Annals of Oncology, 2006, 17(Suppl. 7): vii41-vii45.
K. Katsuragi et al., "Prognostic impact of PCR-based identification of isolated tumour cells in the peritoneal lavage fluid of gastric cancer patients who underwent a curative R0 resection", British Journal of Cancer, 2007, 97: 550-556.
M Inokuchi, et al., "Quantitative evaluation of metastases in axillary lymph nodes of breast cancer, " British Journal of Cancer, 2003 p. 1750-1756, vol. 89.
Susan Frackman et al, "Betaine and DMSO: Enhancing Agents for PCR", Promega Notes, 1998, 65: 27.
Matsuura et al., "Novel molecular diagnostic method for rapid evaluation of lymph node metastasis in breast cancer", Poster Presented at: 28th Annual San Antonio Breast Cancer Symposium, Dec. 8-11, 2005, San Antonio TX,USA.
Michael Mitas, et al., "Quantitative Real-Time RT-PCR Detection of Breast Cancer Micrometastasis Using a Multigene Marker Panel", Int. J. Cancer, 2001, 93: 162-171.
Kiyomi Taniyama et al, "Combination analysis of a whole lymph node by one-step nucleic acid amplification and histology micrometastasis", Pathobiology, 2006, 73(4): 183-191.
Masahiko Tsujimoto et al, "One-step nucleic acid amplification for intraoperative detection of lymph node metastasis in breast cancer patients", Clinical Cancer Research, 2007, 13(16): 4807-4816.
H.Y. Wang et al., "Micrometastases detected by cytokeratin 19 express in sentinel lymph nodes of patients with early-stage cervical cancer", International Journal of Gynecological Cancer, 2006, 16(2): 643-648.
Final Office Action issued on Aug. 27, 2010 in U.S. Appl. No. 11/808,325, in the name of Kazuki Nakabayashi et al.

* cited by examiner

*Primary Examiner* — James Martinell
(74) *Attorney, Agent, or Firm* — Sughrue Mion, PLLC

(57) ABSTRACT

The invention provides a method for judging whether cancer cells are present or not in a sample, comprising a obtaining step of obtaining values related to an expression level of a caner marker gene and a housekeeping gene; a first comparing step of comparing the value related to the expression level of the cancer marker gene with a first threshold value; a normalizing step of normalizing the value related to the expression level of the cancer marker gene based on the value related to the expression level of the housekeeping gene; a second comparing step of comparing the normalized value with a second threshold value; and a judging step of judging whether cancer cells are present or not in the sample based on comparison results obtained in the first and second comparing steps, as well as an apparatus for judging whether cancer cells are present or not.

16 Claims, 8 Drawing Sheets

SEQUENCE LISTING

<160> NUMBER OF SEQ ID NOS: 18

<210> SEQ ID NO 1
<211> LENGTH: 22
<212> TYPE: DNA
<213> ORGANISM: Artificial
<220> FEATURE:
<223> OTHER INFORMATION: Primer

<400> SEQUENCE: 1
agacaatcac agtctctgcg ga                                            22

<210> SEQ ID NO 2

-continued

<211> LENGTH: 20
<212> TYPE: DNA
<213> ORGANISM: Artificial
<220> FEATURE:
<223> OTHER INFORMATION: Primer

<400> SEQUENCE: 2
atccttgtcc tccacgggtt                                                 20

<210> SEQ ID NO 3
<211> LENGTH: 14
<212> TYPE: DNA
<213> ORGANISM: Artificial
<220> FEATURE:
<223> OTHER INFORMATION: Primer

<400> SEQUENCE: 3
cctttcctcc tgct                                                       14

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
ccgaagtctc cttttctcca c                                               21

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
cagatcgaag gcctgaagga                                                 20

<210> SEQ ID NO 6
<211> LENGTH: 19
<212> TYPE: DNA
<213> ORGANISM: Artificial
<220> FEATURE:
<223> OTHER INFORMATION: Primer

<400> SEQUENCE: 6
cttggcccct cagcgtact                                                  19

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
ccaaacggat gaaactctga gc                                              22

<210> SEQ ID NO 8
<211> LENGTH: 22
<212> TYPE: DNA
<213> ORGANISM: Artificial
<220> FEATURE:
<223> OTHER INFORMATION: Primer

<400> SEQUENCE: 8

-continued

| | |
|---|---|
| gcagttctgt gagccaaagg tc | 22 |

<210> SEQ ID NO 9
<211> LENGTH: 26
<212> TYPE: DNA
<213> ORGANISM: Artificial
<220> FEATURE:
<223> OTHER INFORMATION: Primer

<400> SEQUENCE: 9

| | |
|---|---|
| tgaaggtcgg tgtgaacgga tttggc | 26 |

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10

| | |
|---|---|
| tgttgggggc cgagttggga ta | 22 |

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11

| | |
|---|---|
| caaatgctgg accaaacaca a | 21 |

<210> SEQ ID NO 12
<211> LENGTH: 22
<212> TYPE: DNA
<213> ORGANISM: Artificial
<220> FEATURE:
<223> OTHER INFORMATION: Primer

<400> SEQUENCE: 12

| | |
|---|---|
| ttcaccttcc caaagaccac at | 22 |

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13

| | |
|---|---|
| ccacactgtg cccatctacg | 20 |

<210> SEQ ID NO 14
<211> LENGTH: 26
<212> TYPE: DNA
<213> ORGANISM: Artificial
<220> FEATURE:
<223> OTHER INFORMATION: Primer

<400> SEQUENCE: 14

| | |
|---|---|
| aggatcttca tgaggtagtc agtcag | 26 |

<210> SEQ ID NO 15
<211> LENGTH: 21
<212> TYPE: DNA
<213> ORGANISM: Artificial
<220> FEATURE:

```
<223> OTHER INFORMATION: Primer

<400> SEQUENCE: 15
aagaagtcca agctggagtt c                                              21

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
gttggtctgg aattctgtca g                                              21

<210> SEQ ID NO 17
<211> LENGTH: 15
<212> TYPE: DNA
<213> ORGANISM: Artificial
<220> FEATURE:
<223> OTHER INFORMATION: TaqMan-Probe

<400> SEQUENCE: 17
agctgcccaa gccct                                                     15

<210> SEQ ID NO 18
<211> LENGTH: 26
<212> TYPE: DNA
<213> ORGANISM: Artificial
<220> FEATURE:
<223> OTHER INFORMATION: TaqMan-Probe

<400> SEQUENCE: 18
atgccctccc ccatgccatc ctgcgt                                         26
```

METHOD AND APPARATUS FOR JUDGING THE PRESENCE OR ABSENCE OF CANCER CELL

FIELD OF THE INVENTION

The present invention relates to a method and apparatus for judging the presence or absence of cancer cells in a sample containing cells collected from a patient, particularly a patient suspected of having cancer metastasis.

BACKGROUND

Examination of the presence or absence of cancer cells in a sample collected from a patient can be an indicator for judging cancer metastasis in a tissue or organ from which the sample was collected. For judging the presence or absence of cancer cells in a sample, histological cytodiagnosis such as Papanicolaou staining has conventionally been used. In this method, however, there are problems such as a difference in diagnostic result due to the experience of a person who makes the diagnosis, necessity for a long time in examination, and the like.

Accordingly, studies on molecular pathological diagnosis of cancer by LAMP (loop-mediated isothermal amplification method) and PCR (polymerase chain reaction) have been extensively conducted. Pathological molecular diagnosis can be carried out by detecting a cancer marker gene contained in a tissues and cell (for example, an mRNA of a protein expressed specifically in a cancer cell (hereinafter, also referred to simply as cancer marker)). For example, mRNAs of cytokeratin 19 (CK19) and carcinoembryonic antigen (CEA) are known to be effective as cancer marker genes for judging lymph node metastasis of breast cancer. An mRNA of CEA is also known to be effective as a cancer marker for judging metastasis of stomach cancer. These cancer markers are molecules recognized to be significantly different in expression level between a normal sample and a sample containing cancer cells metastasizing to it.

A judgment result of the presence or absence of cancer cells, obtained on the basis of the expression level of a cancer marker, can serve as an indicator for a physician for example to make a diagnosis for metastasis of cancer cells to a specific tissue in a patient.

Conventionally, when such molecular examination is conducted, the expression level of a cancer marker to be analyzed is subjected to conversion (normalization) to the expression level thereof per cell because the number of cells varies from sample to sample. Then, the normalized expression level of the cancer marker in a sample is compared with a threshold value, thereby judging the presence or absence of cancer cells. Specifically, the expression level of a cancer marker gene is divided by the expression level of a housekeeping gene (that is, a gene estimated to be expressed at a constant level in many tissues and cells), thereby normalizing the expression level of the cancer marker gene with the expression level of the housekeeping gene (M. Inokuchi et al., British Journal of Cancer (2003) 89, 1750-1756).

U.S. Publication No. 2007264635 describes a method of obtaining information for prediction of cancer relapse, which comprises amplification reaction of a predetermined gene by PCR and measurement of its amplification product. More specifically, this publication discloses judgment of stomach cancer relapse by normalizing a measurement result with β-actin in Example 4 and judgment of relapse without normalization in Example 5, respectively.

SUMMARY

The scope of the present invention is defined solely by the appended claims, and is not affected to any degree by the statements within this summary.

The present invention provides a method for judging whether a cancer cell exists or not in a sample including a cell obtained from a patient, comprising: an obtaining step of obtaining a value related to an expression level of a cancer marker gene and a value related to an expression level of a housekeeping gene; a first comparing step of comparing the value related to the expression level of the cancer marker gene with a first threshold value; a normalizing step of normalizing the value related to the expression level of the cancer marker gene based on the value related to the expression level of the housekeeping gene, when the value related to the expression level of the cancer marker gene is less than the first threshold value in the first comparing step; a second comparing step of comparing the normalized value obtained from the normalizing step with a second threshold value; and a judging step of judging whether the cancer cell exists or not in the sample based on a comparison result of the first comparing step or the second comparing step.

The present invention also provides a method for judging whether a cancer cell exists or not in a sample including a cell obtained from a patient, comprising: an obtaining step of obtaining a value related to an expression level of a cancer marker gene and a value related to an expression level of a housekeeping gene; a first comparing step of comparing the value related to the expression level of the cancer marker gene with a first threshold value; a normalizing step of normalizing the value related to the expression level of the cancer marker gene based on the value related to the expression level of the housekeeping gene, when the value related to the expression level of the cancer marker gene is less than the first threshold value in the first comparing step; a second comparing step of comparing the normalized value obtained from the normalizing step with a second threshold value; and a judging step of judging whether the cancer cell exists or not in the sample based on a comparison result of the first comparing step or the second comparing step.

The present invention also provides an apparatus for judging whether a cancer cell exists or not in a sample including a cell obtained from a patient, comprising: a measuring part for measuring the sample in order to obtain a value related to an expression level of a cancer marker gene and a value related to an expression level of a housekeeping gene in the sample; and a controller including a memory under control of a processor, the memory storing instructions enabling the processor to carry out operations, comprising: an obtaining step of obtaining the value related to the expression level of the cancer marker gene and the value related to the expression level of the housekeeping gene; a first comparing step of comparing the value related to the expression level of the cancer marker gene with a first threshold value; a normalizing step of normalizing the value related to the expression level of the cancer marker gene based on the value related to the expression level of the housekeeping gene; a second comparing step of comparing the normalized value obtained from the normalizing step with a second threshold value; a judging step of judging whether the cancer cell exists or not in the sample based on comparison results of the first comparing step and the second comparing step; and an output step of outputting a judgment result obtained from the judging step.

The present invention also provides an apparatus for judging whether a cancer cell exists or not in a sample including a cell obtained from a patient, comprising: a measuring part for measuring the sample in order to obtain a value related to an expression level of a cancer marker gene and a value related to an expression level of a housekeeping gene in the sample; and a controller including a memory under control of a processor, the memory storing instructions enabling the processor to carry out operations, comprising: an obtaining step of obtaining the value related to the expression level of the cancer marker gene and the value related to the expression level of the housekeeping gene; a first comparing step of comparing the value related to the expression level of the cancer marker gene with a first threshold value; a normalizing step of normalizing the value related to the expression level of the cancer marker gene based on the value related to the expression level of the housekeeping gene, when the value related to the expression level of the cancer marker gene is less than the first threshold value in the first comparing step; a second comparing step of comparing the normalized value obtained from the normalizing step with a second threshold value; a judging step of judging whether the cancer cell exists or not in the sample based on a comparison result of the first comparing step or the second comparing step; and an output step of outputting a judgment result obtained from the judging step.

DETAILED DESCRIPTION OF THE EMBODIMENT

Figure 1:
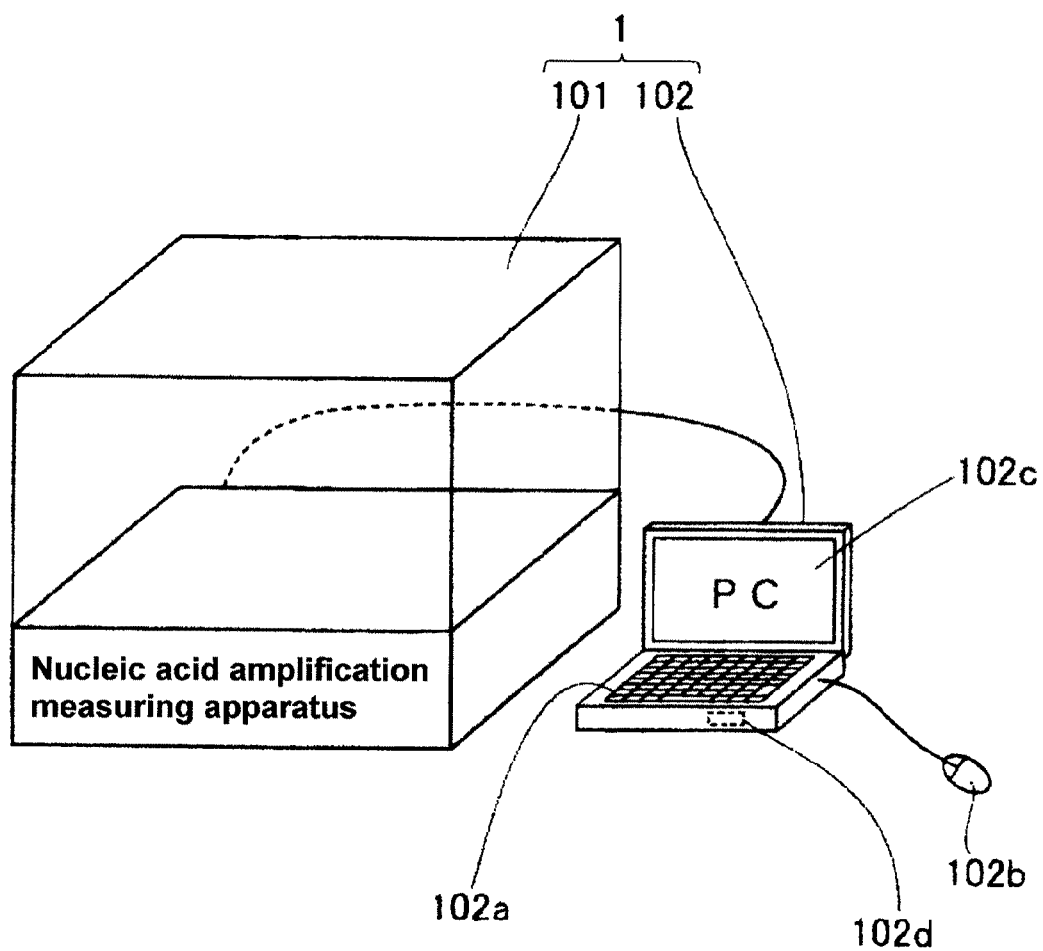
FIG. 1 is a perspective view showing the entire construction of a judging apparatus in accordance with one embodiment of the present invention.

The method in the present embodiment is a method of judging the presence or absence of cancer cells in a sample containing cells collected from a patient. The patient is preferably a patient intended to judge the presence or absence of cancer cells, particularly a patient intended to judge cancer metastasis. Cells obtained from the patient are preferably cells contained in a lymph node tissue, blood or a body cavity wash.

Particularly, the conditions of a body cavity wash may be worse. The body cavity wash is often used in measurement after passage of time after collection, so the conditions of the sample may be further deteriorated. Accordingly, the method in the present embodiment is useful as a method for judging the presence or absence of cancer cells contained in the body cavity wash.

The body cavity wash is a fluid obtained generally by washing a body cavity around a cancerous lesion with physiological saline, in order to examine the presence or absence of cancer metastasis. The body cavity wash obtained from a patient includes an abdominal cavity wash, a thoracic cavity wash, and the like. The abdominal cavity wash includes a subhepatic wash, a left subdiaphragmatic wash, a Douglas pouch wash, and the like.

Preferably, the sample is further treated to give a measurement sample subjected to measurement.

When the sample is a lymph node tissue, the measurement sample can be obtained by treating a lymph node tissue with a treatment solution. The treatment solution preferably contains DMSO (dimethylsulfoxide). The concentration of DMSO in the treatment solution is preferably about 5 to 30% by volume, more preferably about 10 to 25% by volume.

When the sample is a body cavity wash, a nucleic acid extract obtained from a cell suspension that is a concentrate of cells in the body cavity wash can be used as the measurement sample. The cell suspension can be obtained by concentrating cells in a body cavity wash through centrifugation or the like. The nucleic acid extract can be obtained by treating the cell suspension by a nucleic acid extraction method known in the art. A sample obtained by treating the cell suspension with the treatment solution can also be used as a measurement sample. Nucleic acids in the body cavity wash as a sample have often been destroyed. Accordingly, the nucleic acid extract is preferably used as a measurement sample.

The treatment solution may contain a buffer, a surfactant etc. as necessary in addition to DMSO.

The buffer is not limited as long as the pH of the treatment solution can be kept in the range of about 2.5 to 5.0, and examples thereof include glycine-HCl buffer etc. The concentration of the buffer is not particularly limited insofar as the pH of the treatment solution can be kept in the above-mentioned range.

The surfactant is not particularly limited as far as it is a surfactant used ordinarily in the art, but the surfactant is preferably a nonionic surfactant, more preferably a polyoxyethylene nonionic surfactant. The surfactant is particularly preferably a polyoxyethylene nonionic surfactant represented by the following formula:

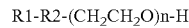

wherein R1 is an alkyl, alkenyl, alkynyl or isooctyl group having 10 to 22 carbon atoms; R2 is —O— or —($C_6H_4$)—O—; n is an integer of 8 to 120. Specific examples of the polyoxyethylene nonionic surfactant include polyoxyethylene lauryl ether, polyoxyethylene cetyl ether, polyoxyethylene oleyl ether, polyoxyethylene myristyl ether, polyoxyethylene stearyl ether, polyoxyethylene nonyl phenyl ether, and polyoxyethylene isooctyl phenyl ether. More specifically, Brij35 (polyoxyethylene (35) lauryl ether) and the like are suitable. The concentration of the surfactant is not particularly limited as long as it is a concentration used ordinarily in the art. For example, the concentration of the surfactant in the treatment solution is preferably 0.1 to 6% by volume, more preferably 1 to 5% by volume.

The mixing ratio of the treatment solution to a lymph node tissue or a cell suspension is not particularly limited. For example, about 0.0001 to 0.005 mL of the treatment solution can be added to and mixed with 1 mg lymph node tissue. This mixing though not particularly limited can be carried out for example for such a time as to mix the lymph node tissue with the treatment solution sufficiently at room temperature.

After the lymph node tissue is mixed with the treatment solution containing DMSO, the lymph node tissue is preferably disrupted. The method of disrupting the lymph node tissue includes homogenization by repeated suction and discharge through a syringe, homogenization with a homogenizer, and a freezing/thawing method. The homogenizer that can be used in the invention is the one used ordinarily in the art and includes, for example, a Waring blender, a Potter-Elvehjem homogenizer, a polytron homogenizer, a Dounce homogenizer, a French press and an ultrasonic disintegrator. Conditions for disruption are suitably established depending on the method and apparatus used and may be those conditions used ordinarily in the art.

A disruption solution of the cells disrupted by the method described above can be partially purified by usual purification methods such as centrifugation, filtration and column chromatography. Depending on the type of a marker gene to be detected, the partially purified solution may be further purified by a method such as a nucleic acid extraction method.

In the obtaining step in the method in the present embodiment, values related respectively to expression levels of a cancer marker gene and a housekeeping gene in the sample are obtained.

In this specification, the "cancer marker gene" refers to a molecular marker gene that occurs at a significantly higher expression level in a cancer cell than in a normal cell. Accordingly, the cancer marker gene is preferably a nucleic acid such as mRNA or DNA, more preferably mRNA.

The cancer marker gene is preferably a gene of a protein such as cytokeratin (CK) (for example CK18, CK19 or CK20), carcinoembryonic antigen (CEA), MUC1 mucin, or mammaglobin (MMG).

The housekeeping gene is not particularly limited as long as it is a gene known to be expressed at a constant level in many cells. The housekeeping gene is preferably a gene of glceyraldehyde-3-phosphate dehydrogenase, cyclophilin, β-actin or α-tubulin.

The values related respectively to the expression levels of the cancer marker gene and the housekeeping gene measured in the obtaining step are values suitably selected depending on the method of measuring the expression level of each gene. The values related to the expression levels of the cancer marker gene and the housekeeping gene are preferably values related to the amounts of mRNAs of the respective genes. The values related to the expression levels of the cancer marker gene and housekeeping gene are preferably values obtained by amplifying the mRNAs by a nucleic acid amplification method. In this case, the values related to the expression levels of the cancer marker gene and housekeeping gene can be optically measured values such as fluorescence intensity, turbidity and absorbance measured by amplifying the mRNAs or the corresponding cDNAs with predetermined primers for a predetermined time, or the time or the number of PCR cycles repeated until predetermined fluorescence intensity, turbidity or absorbance is reached during amplification of the mRNAs or the corresponding cDNAs with predetermined primers.

The nucleic acid amplification method can be carried out according to a method used ordinarily in the art. Particularly, a nucleic acid amplification method based on LAMP (loop-mediated isothermal amplification method) or PCR (polymerase chain reaction) is preferable. When the mRNAs of the cancer marker gene and housekeeping gene are amplified by the nucleic acid amplification method, it is possible to employ a nucleic acid amplification method (for example, RT-PCR or RT-LAMP) involving a reverse transcription reaction before the nucleic amplification reaction.

The nucleic acid amplification method can be carried out specifically by adding primers for amplifying cDNA corresponding to the cancer marker gene or housekeeping gene, an RNA-dependent DNA polymerase (reverse transcriptase), a DNA-dependent DNA polymerase (hereinafter also referred to merely as DNA polymerase) etc. to the sample to prepare a reaction solution, followed by nucleic acid amplification, to determine a value related to the amplified cDNA.

Conditions for the reverse transcription reaction and nucleic acid amplification reaction can vary suitably depending on sequences of the cancer marker gene and housekeeping gene as the templates and sequences of primers. Conditions used in the reverse transcription reaction and nucleic acid amplification reaction may be those described in, for example, Sambrook, J. et al. (1989) Molecular Cloning: A Laboratory Manual (2nd ed.), Cold Spring Harbor Laboratory Press, New York.

Sequences of the primers for amplifying cDNAs corresponding to the cancer marker gene and housekeeping gene can be suitably selected depending on sequences of the cancer marker gene and housekeeping gene. The primer is preferably 5 to 100 nucleotides in length, more preferably 10 to 50 nucleotides in length. The primer can be produced by nucleic acid synthesis methods known in the art.

Preferable examples of the primers for amplifying cDNAs corresponding to the cancer marker gene and housekeeping gene are shown in Table 1 below.

TABLE 1

| Gene Name | | Primer Sequence | SEQ ID NO |
|---|---|---|---|
| Carcinoembryonic antigen (CEA) | forward | 5'-agacaatcacagtctctgcgga-3' | 1 |
| | reverse | 5'-atccttgtcctccacgggtt-3' | 2 |
| MUC1 mucin | forward | 5'-cctttcctcctgct-3' | 3 |
| | reverse | 5'-ccgaagtctccttttctccac-3' | 4 |
| Cytokeratin 19 (CK19) | forward | 5'-cagatcgaaggcctgaagga-3' | 5 |
| | reverse | 5'-cttggcccctcagcgtact-3' | 6 |
| Mammaglobin (MMG) | forward | 5'-ccaaacggatgaaactctgagc-3' | 7 |
| | reverse | 5'-gcagttctgtgagccaaaggtc-3' | 8 |
| Glyceraldehyde-3-phosphate dehydrogenase (GAPDH) | forward | 5'-tgaaggtcggtgtgaacggatttggc-3' | 9 |
| | reverse | 5'-tgttggggccgagttgggata-3' | 10 |
| Cyclophilin | forward | 5'-caaatgctggaccaaacacaa-3' | 11 |
| | reverse | 5'-ttcaccttcccaaagaccacat-3' | 12 |

TABLE 1-continued

| Gene Name | | Primer Sequence | SEQ ID NO |
|---|---|---|---|
| β-Actin | forward | 5'-ccacactgtgcccatctacg-3' | 13 |
| | reverse | 5'-aggatcttcatgaggtagtcagtcag-3' | 14 |
| α-Tubulin | forward | 5'-aagaagtccaagctggagttc-3' | 15 |
| | reverse | 5'-gttggtctggaattctgtcag-3' | 16 |

The primer sequences are not limited to those shown in Table 1, and those skilled in the art can select suitable primers from known sequences of the whole of these genes.

The primers may be modified by techniques ordinarily used in the art. Labeling of the primers can be conducted using a radioactive element or a nonradioactive molecule. The radioisotope that can be used in the invention includes $^{32}P$, $^{33}P$, $^{35}S$, $^{3}H$ and $^{125}I$. The nonradioactive substance is selected from ligands such as biotin, avidin, streptavidin and digoxigenin; haptens; dyes; and luminescent reagents such as radioluminescent, chemiluminescent, bioluminescent, fluorescent or phosphorescent reagents.

Enzymes having a reverse transcription activity and DNA polymerase that can be used in the invention may be those well known in the art. The enzymes having a reverse transcription activity include AMV (Avian Myeloblastosis Virus) reverse transcriptase, M-MLV (Molony Murine Leukemia Virus) reverse transcriptase, etc. The DNA polymerase that can be used in the invention includes Taq DNA polymerase, Pfu DNA polymerase, T4 DNA polymerase and Bst DNA polymerase.

By determining values related to the nucleic acid amplification products formed by the nucleic acid amplification method, values related to the expression levels of the cancer marker gene and housekeeping gene can be determined. When the values related to the expression levels of the cancer marker gene and housekeeping gene are the amounts of mRNAs of the genes, quantitative RT-PCR (Quantitative Reverse Transcription-PCR) and quantitative RT-LAMP (Quantitative Reverse Transcription-LAMP) can be preferably used. According to these methods, the optical states (turbidity, absorbance, fluorescence intensity etc.) of the reaction solution are changed with amplification of the nucleic acids (cDNAs) and can thus be measured in real time to determine the values related to the expression levels of the cancer marker gene and housekeeping gene.

Specific examples of quantitative RT-PCR include an SYBR Green method that involves previously adding SYBR Green to a reaction solution before nucleic acid amplification reaction and measuring, in real time, fluorescence intensity increased with amplification of cDNA during the amplification reaction and a TaqMan™ method that involves amplification reaction with a TaqMan™ probe and then measuring, in real time, fluorescence intensity increased with amplification of cDNA. The values related to the expression levels of the cancer marker gene and housekeeping gene can also be determined as the number of cycles required until the fluorescence intensity of the reaction solution reaches a predetermined level.

When RT-LAMP is used, a large amount of magnesium pyrophosphate is formed as a byproduct accompanying cDNA amplification. Because this magnesium pyrophosphate is insoluble, the reaction solution turns turbid as magnesium pyrophosphate is increased. Accordingly, the turbidity (or absorbance) of the reaction solution can be measured optically in real time to determine the values related to the expression levels of the cancer marker gene and housekeeping gene. The SYBR Green method can also be used in the RT-LAMP method. The values related to the expression levels of the cancer marker gene and housekeeping gene can also be determined as the time required until the turbidity, absorbance, fluorescence intensity or the like of the reaction solution reaches a predetermined level.

The method in the present embodiment comprises a first comparing step of comparing the value related to the expression level of the cancer marker gene obtained in the obtaining step, with a first threshold value. The first threshold value is a value that can be suitably established depending on the type of the cancer marker gene and the method used in the obtaining step, particularly the type of the nucleic acid amplification method. The first threshold value can be set to a value equal to or lower than the value related to the expression level of the cancer marker gene contained in a sample (positive sample) confirmed to contain cancer cells, particularly a sample confirmed to have cancer metastasis and simultaneously to a value higher than the value related to the expression level of the cancer marker gene contained in a sample (negative sample) confirmed to be free from cancer cells, particularly a sample confirmed to be free from cancer metastasis. The first threshold value is set preferably to a value which is obtained by determining values related to the expression levels of the cancer marker gene in a plurality of positive samples and values related to the expression levels of the cancer marker gene in a plurality of negative samples and which is capable of distinguishing positive and negative samples from each other at the highest probability.

One mode of the method in the present embodiment comprises a normalizing step of normalizing the value related to the expression level of the cancer marker gene, by the value related to the expression level of the housekeeping gene obtained in the obtaining step.

In this specification, "normalization" means that the value related to the expression level of the cancer marker gene is converted into a relative value based on the value related to the expression level of the housekeeping gene. Specifically, normalization is conducted by dividing the value related to the expression level of the cancer marker gene by the value related to the expression level of the housekeeping gene.

The method in the present embodiment comprises a second comparing step of comparing the normalized value obtained in the normalizing step with a second threshold value.

The second threshold value is a value that can be suitably established depending on the type of the cancer marker gene, the type of the housekeeping gene and the method used in the obtaining step, particularly the type of the nucleic acid amplification method. The second threshold value can be set to a value equal to or lower than a normalized value obtained by normalizing the value related to the expression level of the cancer marker gene contained in a sample (positive sample) confirmed to contain cancer cells, particularly a sample confirmed to have cancer metastasis, by the value related to the expression level of the housekeeping gene in the positive sample and simultaneously to a value higher than a normalized value obtained by normalizing the value related to the expression level of the cancer marker gene contained in a sample (negative sample) confirmed to be free from cancer cells, particularly a sample confirmed to free from cancer metastasis, by the value related to the expression level of the housekeeping gene in the negative sample. The second threshold value is set preferably to a value which is obtained by determining normalized value of the values related to the expression levels of the cancer marker gene in a plurality of positive samples and normalized values of the values related to the expression levels of the cancer marker gene in a plurality of negative samples and which is capable of distinguishing positive and negative samples from each other at the highest probability.

The method in the present embodiment comprises a judging step of judging whether cancer cells exist or not in the sample based on comparison results obtained in the first comparing step and the second comparing step.

It is preferable in the judging step that cancer cells are judged to be present in the sample when the value related to the expression level of the cancer marker gene in the first comparing step is equal to or higher than the first threshold value, and/or the normalized value in the second comparing step is equal to or higher than the second threshold value.

That is, it is preferable that cancers cells are judged to be present in the sample in any of the following cases:
Case (A) where the comparison result in the first comparing step is:
(value related to the expression level of the cancer marker gene)$\geq$(first threshold value), while the comparison result in the second comparing step is:
(normalized value)<(second threshold value);
Case (B) where the comparison result in the first comparing step is:
(value related to the expression level of the cancer marker gene)<(first threshold value), while the comparison result in the second comparing step is:
(normalized value)$\geq$(second threshold value); and
Case (C) where the comparison result in the first comparing step is:
(value related to the expression level of the cancer marker gene)$\geq$(first threshold value), and the comparison result in the second comparing step is:
(normalized value)$\geq$(second threshold value).

Another mode of the present embodiment comprises a first judging step of judging whether cancer cells are present or not in the sample based on a comparison result obtained in a fist comparing step and a second judging step of judging whether cancer cells are present or not in the sample based on a comparison result obtained in a second comparing step.

In the first judging step, cancer cells are judged to be present in the sample when the value related to the expression value of the cancer marker gene in the first comparing step is equal to or higher than the first threshold value.

In the second judging step, cancer cells are judged to be present in the sample when the normalized value in the second comparing step is equal to or higher than the second threshold value.

In still another mode of the present embodiment, when the value related to the expression level of the cancer marker gene is lower than the first threshold value in the first comparing step, the normalizing step and the second comparing step are carried out. In this mode, cancer cells can be judged to be present in the sample when the expression level of the cancer marker gene is higher than the first threshold value in the first comparing step, and therefore, the normalizing step and the second comparing step using a normalized value are not carried out.

Figure 4:
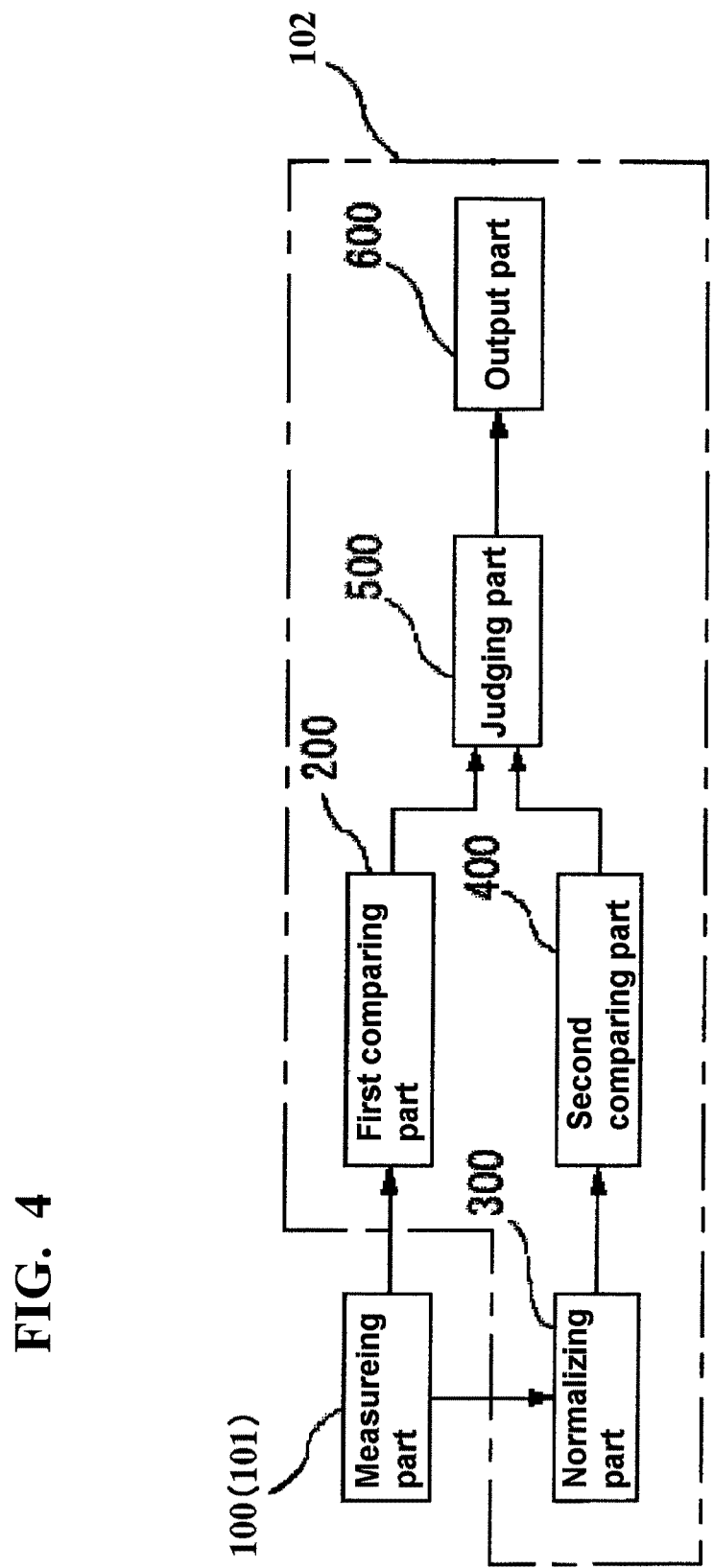
FIG. 4 is a block diagram showing a judging apparatus in accordance with one embodiment of the present invention.

An apparatus for judging the presence or absence of cancer cells, which is used for carrying out the method for judging the presence or absence of cancer cells, is also one aspect of the present embodiment. FIG. 4 is a block diagram showing the apparatus in the present embodiment.

As shown in FIG. 4, the apparatus in the present embodiment includes:
a measuring part 100 for measuring the sample in order to obtain a value related to the expression level of a cancer marker gene and a value related to the expression level of a housekeeping gene in the sample containing cells collected from a patient;
a first comparing part 200 for comparing the value related to the expression level of the marker gene obtained based on a measuring result of the measuring part, with a first threshold value;
a normalizing part 300 for normalizing the expression level of the cancer marker gene, on the basis of the value related to the expression level of the housekeeping gene obtained from the measuring result of the measuring part;
a second comparing part 400 for comparing the normalized value obtained in the normalizing part with a second threshold value;
a judging part 500 for judging whether cancer cells are present or not in the sample based on comparison results obtained in the first comparing part and the second comparing part; and
an output part 600 for outputting a judgment result obtained in the judging part.

The measuring part 100 is not particularly limited as long as it can measure the sample for obtaining the value related to the expression level of the cancer marker gene and the value related to the expression level of the housekeeping gene. The measuring part is preferably a nucleic acid amplification measuring apparatus that can measure nucleic acids amplified by the nucleic acid amplification methods such as LAMP method and PCR method. The measuring part is particularly preferably a nucleic acid amplification measuring apparatus for optically measuring nucleic acid amplification products obtained by amplifying the cancer marker gene and housekeeping gene in a sample by primers and a nucleic acid amplification enzyme.

The first comparing part 200, the normalizing part 300, the second comparing part 400, the judging part 500 and the output part 600 can be constituted by a personal computer (PC) 102 connected to the measuring part 100. In this case, the personal computer (PC) 102 comprises a controller 102 (d) controlling the measuring part 100 (FIG. 1). The controller 102 (d) includes CPU (central processing unit), RAM, ROM and a memory etc. the memory stores instructions enabling the CPU to carry out operations for (1) obtaining the value related to the expression level of the cancer marker gene and the value related to the expression level of the housekeeping gene from the measureing part 100, (2) comparing the expression level of the cancer marker gene obtained from the measuring result of the measuring part 100 with a first threshold, (3) normalizing the expression level of the cancer marker gene on the basis of the value related to the expression level of the housekeeping gene obtained from the measuring result of the measuring part, (3) comparing the resulting normalized value with a second threshold value, (3) judging the presence or absence of cancer cells in the sample on the basis of these comparison results, and outputting a judgment result to a display 102c.

The output part 600 is not particularly limited as long as it can output the judgment result obtained in the judging part 500, and examples of the output part include a printing part, a display, and an audio output part. Specifically, the output part maybe a monitor, printer or speaker connected to the judging part, preferably a monitor.

The apparatus in the present embodiment may further include a measurement sample preparing part for preparing the measurement sample described above. The measurement sample preparing part preferably includes a cell concentration part for concentrating cells in a sample (for example, a centrifugal part), a nucleic acid extraction part for extracting nucleic acids from cells, and a nucleic acid concentration part for concentrating the obtained nucleic acids.

Figure 2:
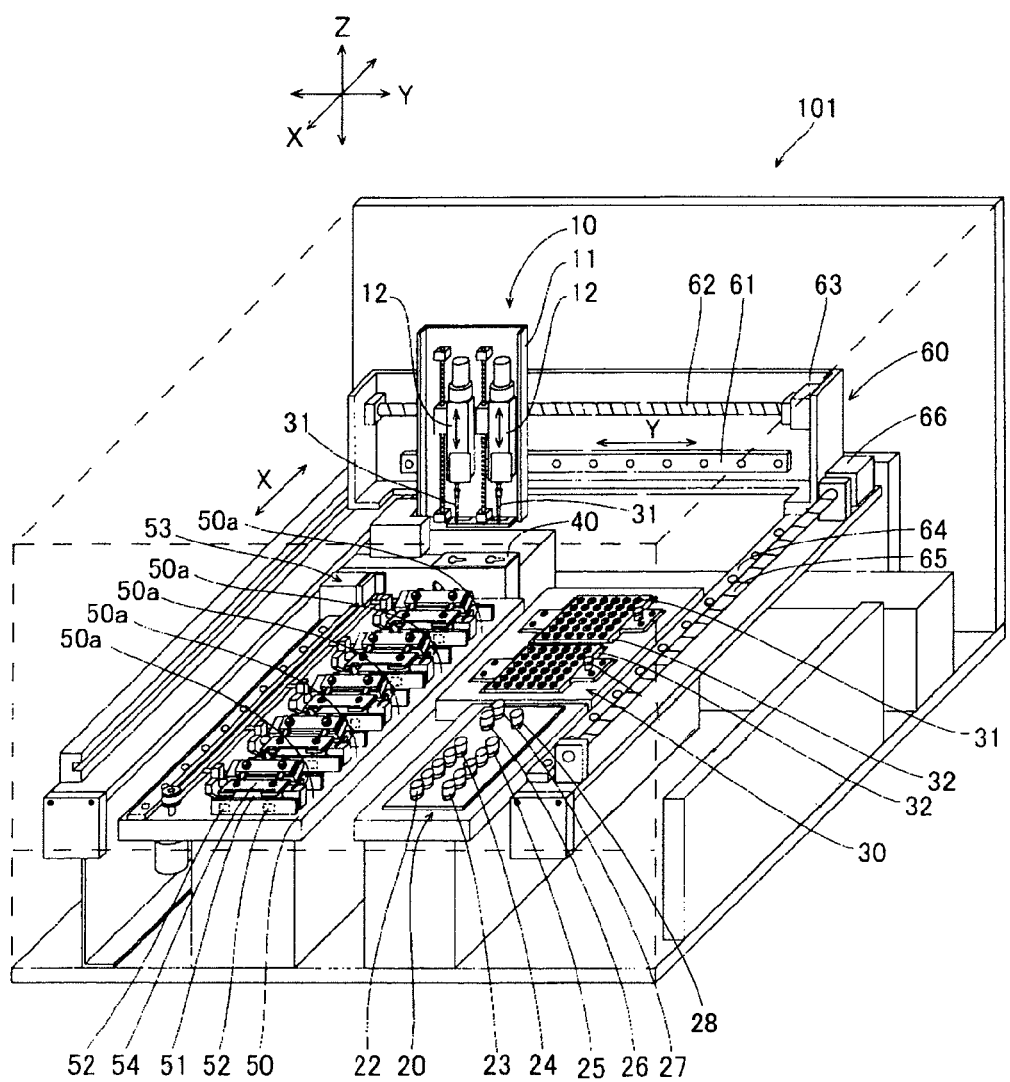
FIG. 2 is a perspective view showing the entire construction of a nucleic acid amplification measuring apparatus as a measurement part of the judging apparatus shown in FIG. 1.
Figure 3:
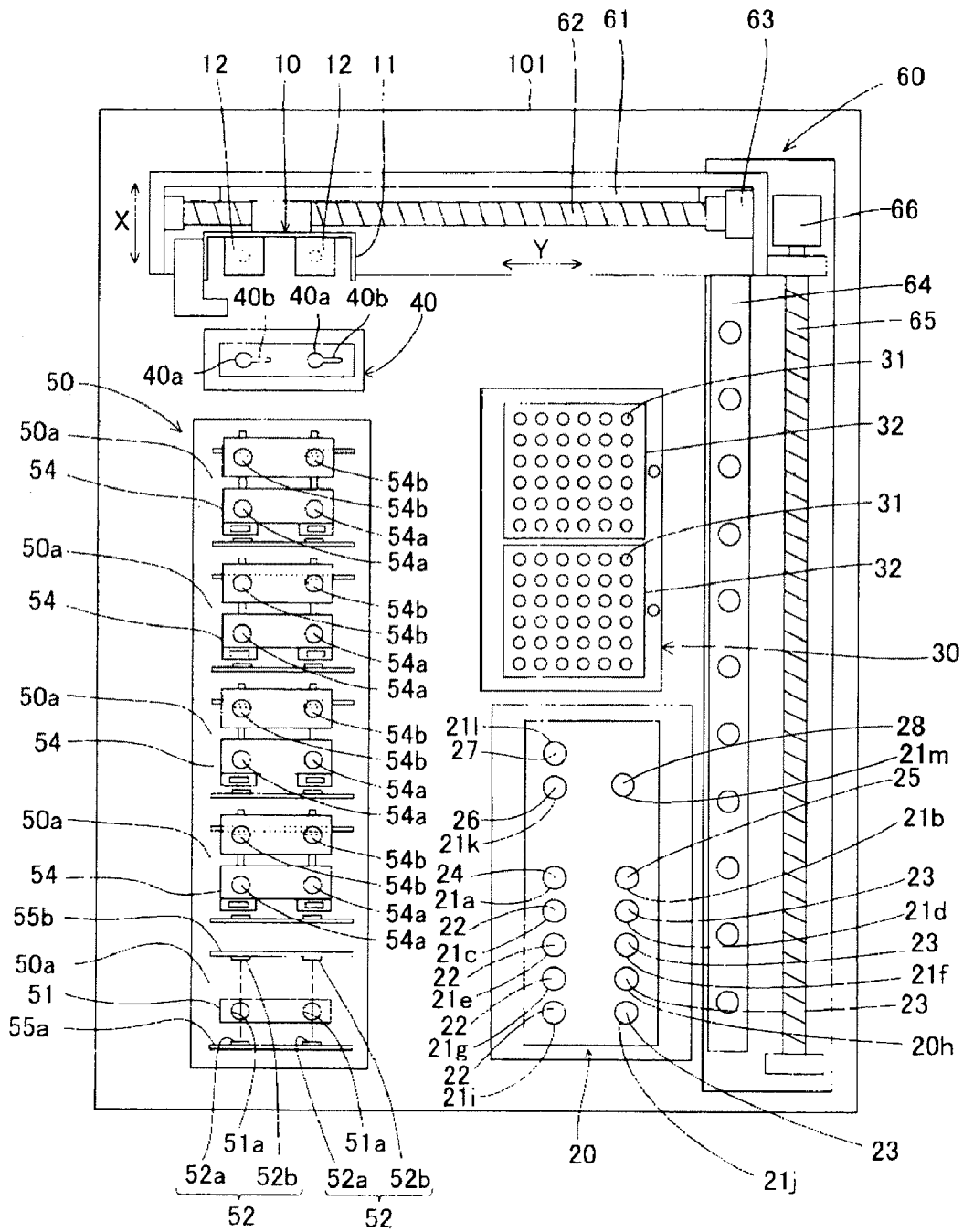
FIG. 3 is a schematic plane view of the nucleic acid amplification measuring apparatus in FIG. 2.

One embodiment of the apparatus for judging cancer metastasis according to the present invention is shown in FIGS. 1 to 3. FIG. 1 is a perspective view showing the entire constitution of the judging apparatus according to one embodiment of the present invention. FIG. 2 is a perspective view showing the entire constitution of a nucleic acid amplification measuring apparatus as the measuring part shown in FIG. 1. FIG. 3 is a schematic plan view of the nucleic acid amplification measuring apparatus in FIG. 2.

As shown in FIG. 1, the judging apparatus 1 in one embodiment of the present invention may be composed of a nucleic acid amplification measuring apparatus 101 and a personal computer (PC) 102 connected to the nucleic acid amplification measuring apparatus to enable communication therebetween with or without a line. The personal computer (PC) 102 functions as the first comparing part 200, the second comparing part 400, the normalizing part 300, the judging part 500 and the output part 600.

As shown in FIG. 2, the nucleic acid amplification measuring apparatus 101 includes a dispensing mechanical part 10, a sample setting part 20, a chip setting part 30, a chip disposing part 40, a reaction detection part 50 composed of five reaction detection blocks 50a, and a transfer part 60 for transferring the dispensing mechanical part 10 in the X- and Y-axial directions.

As shown in FIG. 2, the dispensing mechanical part 10 includes an arm 11 moving in the X- and Y-axial directions (in the horizontal direction) by way of the transfer part 60 and two syringes 12 that can independently move in the Z-axial direction (in the vertical direction) relative to the arm 11.

As shown in FIGS. 2 and 3, the sample setting part 20 is provided with ten sample container setting holes 21a to 21j, one enzyme reagent container setting hole 21k, and one primer reagent container setting hole 21l in the order from the front of the apparatus. The ten sample container setting holes 21a to 21j are arranged in 2 lines each having the 5 holes. Then, the sample container setting holes 21c and 21d, the sample container setting holes 21e and 21f, the sample container setting holes 21g and 21h, and the sample container setting holes 21i and 21j are arranged in a sample setting position 1, a sample setting position 2, a sample setting position 3 and a sample setting position 4 respectively in the order from the back of the apparatus.

In the present embodiment, a sample container 22 that has accommodated a measurement sample prepared by treating a sample such as a lymph node tissue or an abdominal cavity wash is set in the sample container setting holes 21c, 21e, 21g and 21i in the left side of the front. A sample container 23 that has accommodated a diluted sample prepared by diluting the measurement sample 10-fold is set in the sample container setting holes 21d, 21f, 21h and 21j in the right side of the front.

A container 24 that has accommodated a positive control for confirming that a nucleic acid that should be amplified is normally amplified is set in the sample container setting hole 21a. A container 25 that has accommodated a negative control for confirming that a nucleic acid that should not be amplified is normally not amplified is arranged in the sample container setting hole 21b.

An enzyme reagent container 26 that has accommodated a nucleic acid amplification enzyme reagent for amplifying nucleic acid is set in an enzyme reagent container setting hole 21k. An enzyme reagent container 27 that has accommodated a primer reagent for amplifying a cDNA corresponding to the mRNA of carcinoembryonic antigen (hereinafter also referred to simply as CEA) is set in a primer reagent container setting hole 21l. A primer reagent container 28 that has accommodated a primer reagent for amplifying a cDNA corresponding to the mRNA of β-actin is set in a primer reagent container setting hole 21m.

As shown in FIGS. 2 and 3, each of the reaction detection blocks 50a in the reaction detection part 50 is composed of a reaction part 51, two turbidity detection parts 52, and a lid closing mechanical part 53 (see FIG. 2). As shown in FIG. 3, the reaction part 51 arranged in each reaction detection block 50a is provided with two detection cell setting holes 51a for setting a detection cell 54. The reaction detection blocks 50a are arranged in a cell setting position 1, a cell setting position 2, a cell setting position 3, a cell setting position 4 and a cell setting position 5 respectively in the order from the back of the apparatus.

The turbidity detecting part 52 is composed of a LED light source 52a consisting of a blue LED having a wavelength of 465 nm attached to a substrate 55a arranged on one side of the reaction part 51 and a photodiode light receiving part 52b attached to a substrate 55b arranged on the other side of the reaction part 51. Each reaction detection block 50a is provided with two sets each consisting of a turbidity detection part 52 including one LED light source 52a and one photodiode light receiving part 52b.

The detection cell 54 has two cell parts 54a for accommodating a measurement sample and two lids 54b for closing the two cell parts 54a.

As shown in FIG. 2, a transfer part 60 includes a translatory guide 61 and a ball screw 62 for transferring the dispensing mechanical part 10 in the Y-axial direction, a stepping motor 63 for driving the ball screw 62, a translatory guide 64 and a ball screw 65 for transferring the dispensing mechanical part 10 in the X-axial direction, and a stepping motor 66 for driving the ball screw 65. The transfer of the dispensing mechanical part 10 in the X- and Y-axial directions is carried out by rotating the ball screws 62 and 65 with the stepping motors 63 and 66, respectively.

As shown in FIG. 1, the personal computer (PC) 102 includes input devices that are keyboard 102a and mouse 102b, the display 102c consisting of a monitor, and the controller 102d for comparing, normalizing and judging the measurement result of a sample. By a command memorized in a memory contained in the personal computer (PC) 102, the controller 102d functions as a first comparing part 200, a second comparing part 400, a normalizing part 300 and a judging part 500. Then, the judgment result obtained in the controller 102d is outputted to a display 102c. That is, the personal computer (PC) 102 functions as a computer system which judges the presence or absence of cancer cells in the measurement sample, on the basis of the measurement result in the nucleic acid amplification measuring apparatus as a measuring part, and outputs the judgment result.

The judging apparatus in the embodiment described above is composed of the nucleic acid amplification measuring apparatus 101 and the personal computer (PC) 102 connected to the nucleic acid amplification measuring apparatus 101, but the functions of the personal computer (PC) 102 maybe integrated in the nucleic acid amplification measuring apparatus 101.

Figure 5:
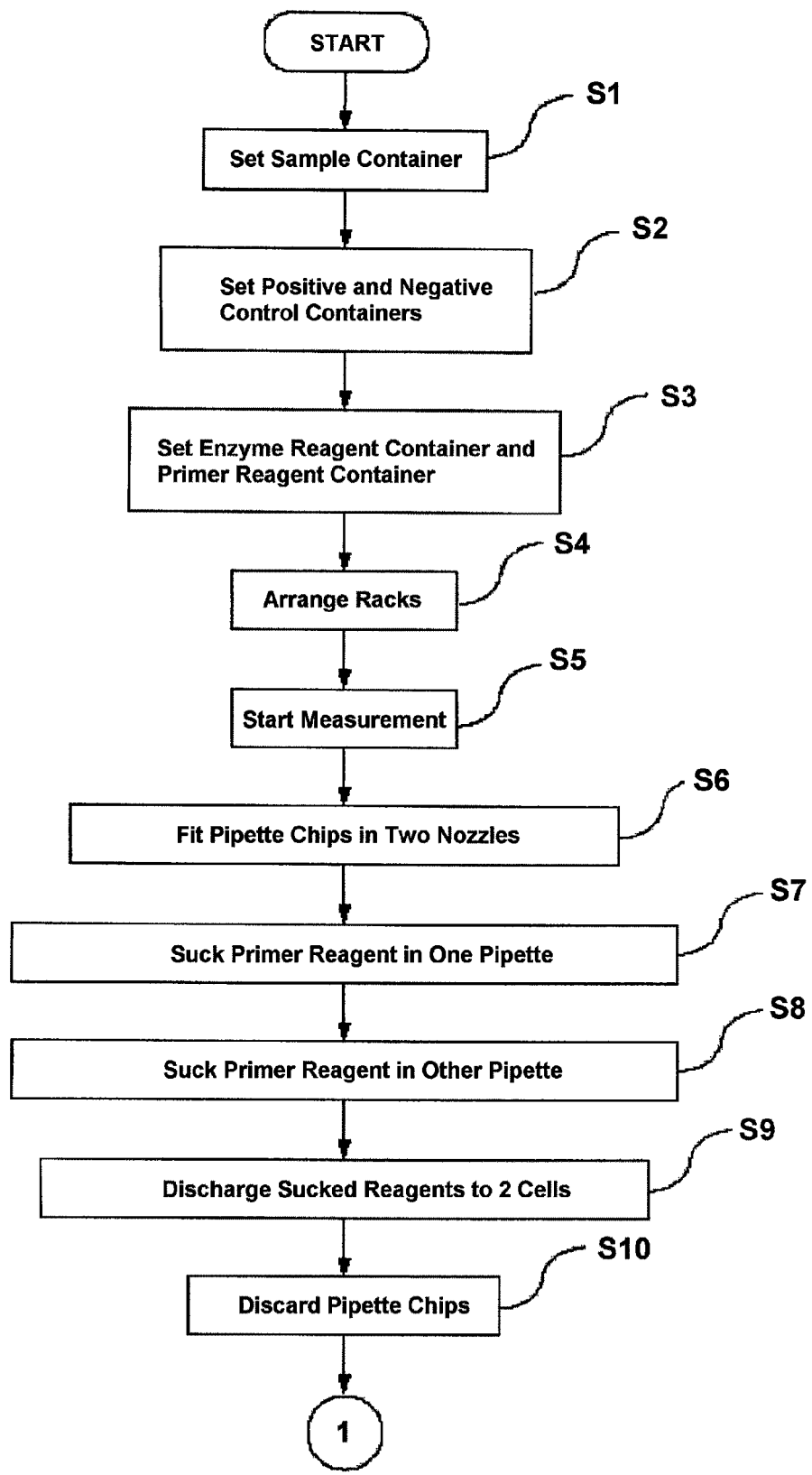
FIG. 5 is a flow chart showing the operation of a judging apparatus in accordance with one embodiment of the present invention.
Figure 6:
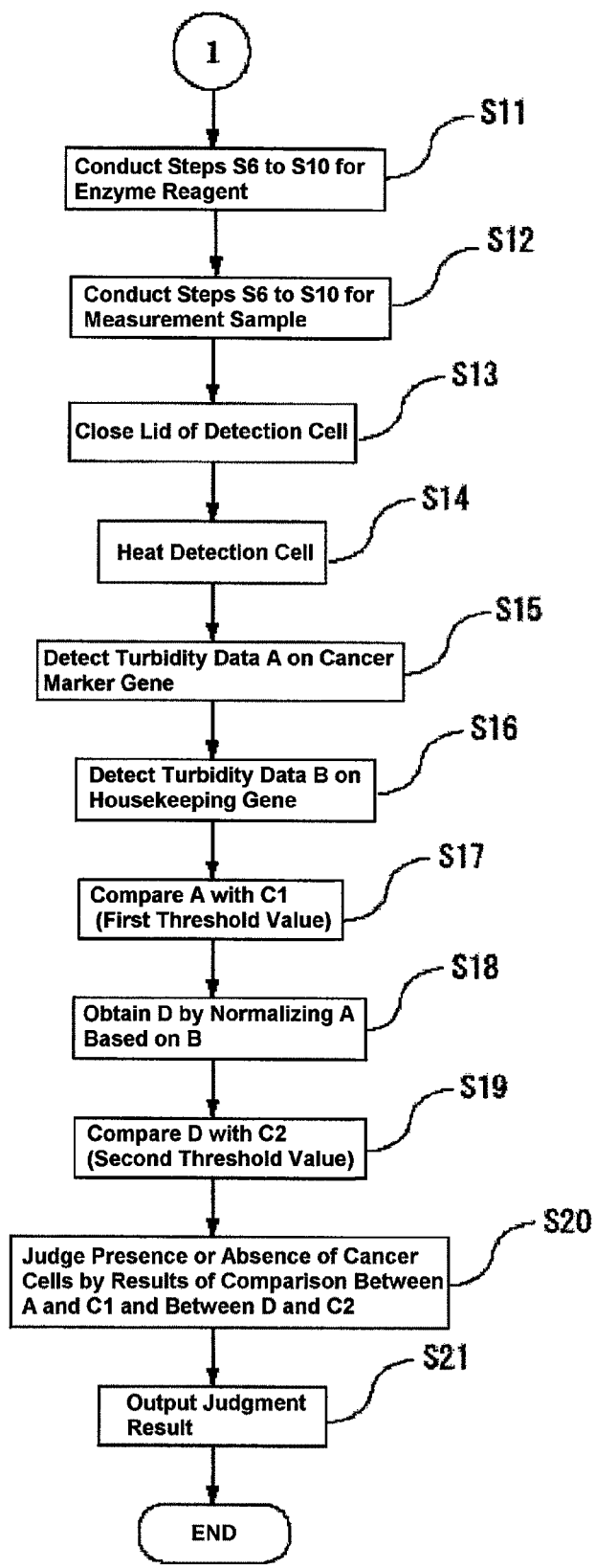
FIG. 6 is a flow chart showing the operation of a judging apparatus in accordance with one embodiment of the present invention.

FIG. 5 is a flow chart showing the operation of a judging apparatus 1 in accordance with the present embodiment. The operation of the judging apparatus 1 is described by reference to FIG. 5. The apparatus described hereafter is an apparatus capable of executing the following steps: 1) a cancer marker gene (CEA) and a housekeeping gene (β-actin) present in an abdominal cavity wash obtained by washing the abdominal cavity of a patient under stomach cancer surgery are amplified by the LAMP method, 2) a change in white turbidity attributable to magnesium pyrophosphate formed accompanying the amplification is measured thereby determining values related to the expression levels of CEA and β-actin, 3) these values are compared with a threshold value, to judge the presence or absence of cancer cells in the abdominal cavity wash, and 4) information for assisting judgment of stomach cancer metastasis is provided. In the following description, the operation in a mechanism for measuring the value related to the expression level of the cancer marker gene is mainly described, but this description also applies to the operation in a mechanism for measuring the value related to the expression level of the housekeeping gene.

As shown in FIGS. 2 and 3, a sample container 22 that has accommodated a measurement sample prepared by treating an abdominal cavity wash (through concentration, nucleic acid extraction, etc.) is set in sample container setting holes 21c to 21j (step S1). Separately, a container 24 that has accommodated a positive control and a container 25 that has accommodated a negative control are set in sample container setting holes 21a and 21b respectively (see FIG. 3) (step S2). An enzyme reagent container 26 that has accommodated a nucleic acid amplification enzyme reagent for nucleic acid amplification, a primer reagent container 27 that has accommodated a primer reagent (CEA primer reagent) for amplification of CEA and a primer reagent container 28 that has accommodated a primer reagent (β-actin primer reagent) for amplification of β-actin are set in an enzyme reagent container setting hole 21k, a primer reagent container setting hole 21l and a primer reagent container setting hole 21l respectively (step S3). Two racks 32 that have accommodated 36 disposable pipette chips 31 are arranged in a chip setting part 30 (step S4).

When the operation of the nucleic acid amplification measuring apparatus 101 is started (step S5), an arm 11 of the dispensing mechanical part 10 is transferred from the initial position to the chip setting part 30 by the transfer part 60 shown in FIG. 2, and in the chip setting part 30, two syringes 12 of the dispensing mechanical part 10 are transferred downward. The tips of the nozzles of the two syringes 12 are pressed into the upper openings of the two pipette chips 31 and thus the pipette chips 31 are automatically fitted into the tips of the nozzles of the two syringes 12 (step S6). Then, the two syringes 12 are transferred upward and then the arm 11 of the dispensing mechanical part 10 is transferred in the X-axial direction to a position above the primer reagent container 27 that has accommodated a CEA primer reagent. Then, one syringe 12 positioned above the primer reagent container 27 is transferred downward, to suck up the CEA primer reagent, and then transferred upward (step S7). Thereafter, the arm 11 of the dispensing mechanical part 10 is transferred in the Y-axial direction by the transfer part 60 until the other syringe 12 is positioned above the same primer reagent container 27. Then, the other syringe 12 is transferred downward, to suck up the CEA primer reagent from the same primer reagent container 27, and then transferred upward (step S8). In this manner, the CEA primer reagent in the primer reagent container 27 is sucked up by the two pipette chips 31 fitted into the syringes 12.

The two syringes 12 that have sucked up the CEA primer reagent are transferred upward, and then the arm 11 of the dispensing mechanical part 10 is transferred by the transfer part 60 to a position above the reaction detection block 50a positioned in the cell setting position 1 in the backmost side (backside of the front of the apparatus). In the reaction detection block 50a in the backmost side, the two syringes 12 are transferred downward, whereby the two pipette chips 31 fitted into the two syringes 12 are inserted respectively into two cell parts 54a of the detection cell 54. Using the syringes 12, the CEA primer reagent is discharged into the two cell parts 54a respectively (step S9).

After the CEA primer reagent is discharged, the two syringes 12 move upward, and then the arm 11 of the dispensing mechanical part 10 is transferred in the X-axial direction to a position above a chip disposing part 40 by the transfer part 60. Then, the pipette chip 31 is disposed of in the chip disposing part 40 (step S10). Specifically, the two syringes 12 are transferred downward, whereby the pipette chips 31 are inserted into two chip disposing holes 40a of the chip disposing part 40 (see FIG. 3). In this state, the arm 11 of the dispensing mechanical part 10 is transferred in the Y-axial direction by the transfer part 60, thereby transferring the pipette chips 31 below groove 40b. Then, the two syringes 12 are transferred upward, whereby a collar element of the upper surface of the pipette chip 31 is abutted against the lower sides of the groove 40b and receives downward force from the lower sides, and thus the pipette chips 31 are automatically detached from the nozzles of the two syringes 12. The pipette chips 31 are thereby disposed of in the chip disposing part 40.

Then, the enzyme reagent is discharged from the enzyme reagent container 26 into the cell part 54a by the same movement (step S11), and the samples are discharged from the sample containers 22 and 23 into the cell parts 54a by the same movement (step S12).

Then, the CEA primer reagent, the enzyme reagent and the sample are discharged into the cell part 54a, and then the lid 54b of the detection cell 54 is closed (step S13). After the lid is closed, the temperature of the liquid in the detection cell 54 is risen from about 20° C. to about 65° C., whereby a cDNA corresponding to the mRNA of CEA as a cancer marker gene is amplified by RT-LAMP (step S14). Then, white turbidity attributable to magnesium pyrophosphate formed accompanying amplification is detected by turbidimetry. Specifically, turbidity data A are detected by detecting (monitoring) the turbidity in the detection cell 54 during amplification reaction, by using a LED light source 52a and a photodiode light receiving part 52b shown in FIG. 3 (step S15).

Separately, turbidity data B related to the expression of a housekeeping gene of β-actin are detected by the same movement as descried above (step S16).

The obtained turbidity data are transmitted in real time from the nucleic acid amplification measuring apparatus 101 to the personal computer (PC) 102. the controller 102d in the personal computer (PC) 102 compares the turbidity data A on the cancer marker gene with a previously determined first threshold C1 (step S17), normalizes the turbidity data A on the cancer marker gene on the basis of the turbidity data B on the housekeeping gene (step S18), compares the resulting normalized value D with a previously determined second threshold C2 (step S19), judges the presence or absence of cancer cells on the basis of the resulting comparison result (step S20), and outputs the judgment result (step S21). On the basis of this outputted result, a physician for example can judge cancer metastasis.

Judgment of the presence or absence of cancer cells in step S20 can be carried out by the same treatment as in the judging step in the present embodiment described above. That is, it is preferable that cancer cells are judged to be present in the measurement sample when the turbidity data A on the cancer marker gene is equal to or higher than the first threshold C1 in step S17, and/or the normalized value D is equal to or higher than the second threshold C2 in step S19.

Specifically, it is preferable that in step S20, cancers cells are judged to be present in the measurement sample in any of the following cases:

Case (A) where the comparison result in step S17 is:
(turbidity data A)≧(first threshold C1), while the comparison result in step S19 is:
(normalized value D)<(second threshold C2);

Case (B) where the comparison result in step S17 is:
(turbidity data A)<(first threshold C1), while the comparison result in step S19 is:
(normalized value D)≧(second threshold C2); and Case (C) where the comparison result in step S17 is:
(turbidity data A)≧(first threshold C1), and the comparison result in step S19 is:
(normalized value D)≧(second threshold C2).

Figure 7:
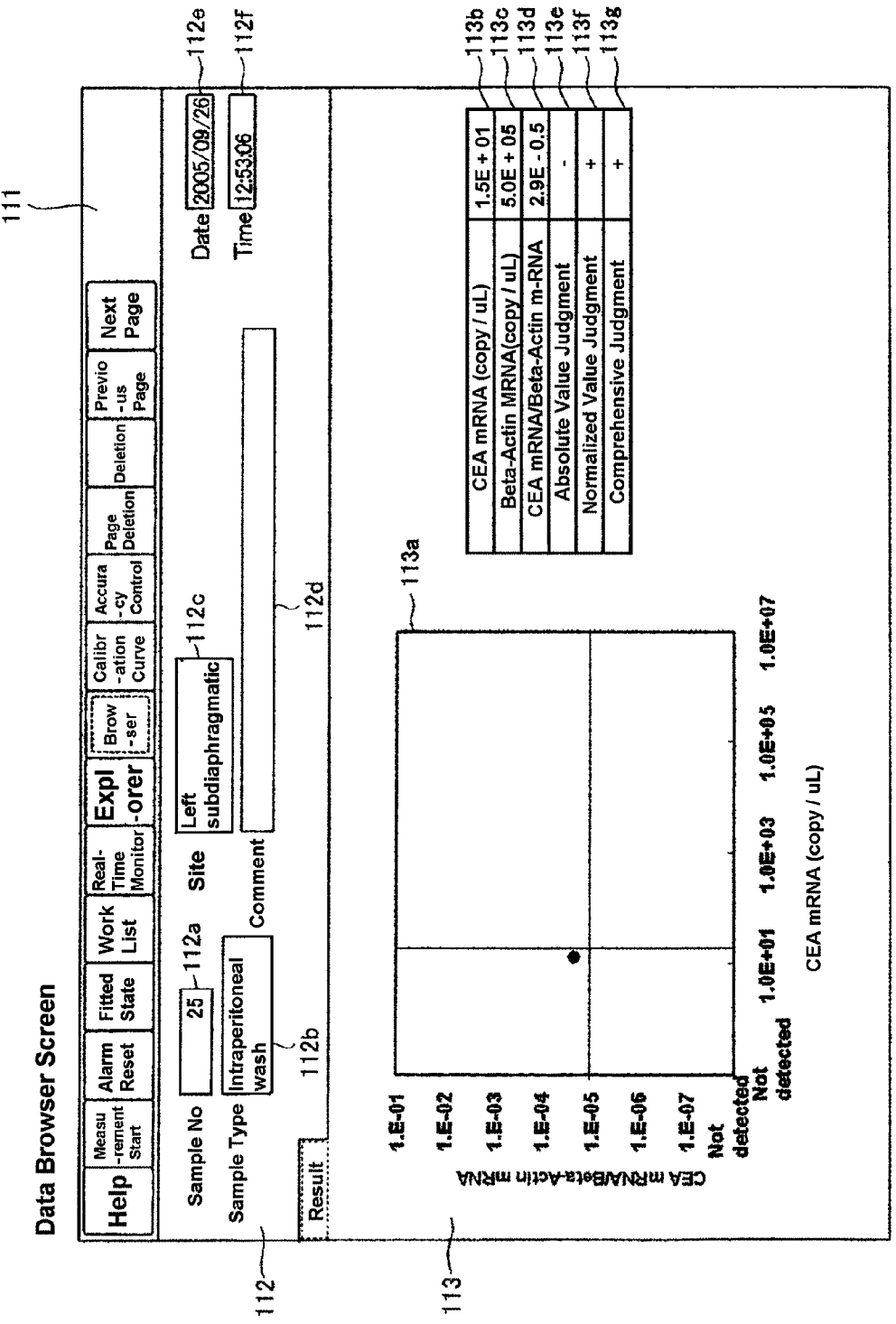
FIG. 7 is a view showing a display example of a display of the judging apparatus of the present invention.

FIG. 7 is a display example of the display 102c shown in FIG. 1. In FIG. 7, 111 is a display area for a toolbar displaying buttons for executing various functions such as help function, 112 is a display area for a measurement sample information display for displaying various information on a measurement sample, and 113 is a display area for a measurement result display for displaying a measurement result of the measurement sample displayed in the measurement sample information display 112.

The measurement sample information display 112 is provided with a sample number display area 112a, a sample type display area 112b, a site display area 112c, a comment display area 112d, a measurement date display area 112e, and a measurement time display area 112f. The sample number display area 112a displays the sample number of a measurement sample used. The sample type display area 112b displays the type of a sample collected from a patient. The type of a sample collected from a patient includes, for example, a lymph node tissue, blood, an abdominal cavity wash, and a thoracic cavity wash. The site display area 112c displays information on the site from which the patient sample is collected. In FIG. 7, "left subdiaphragmatic" for example is displayed on the site display area 112c. From this, it can be known that this measurement sample is a measurement sample prepared from a left subdiaphragmatic abdominal cavity wash. The comment display area 112d displays other information on the measurement sample, which is available for diagnosis of cancer metastasis. The measurement date display area 112e and measurement time display area 112f display the date of measurement of the measurement sample (in the figure, "2005/09/26") and the time of measurement of the measurement sample (in the figure, "12:53:06"), respectively.

The measurement result display 113 is provided with a graph 113a, a first measurement result display area 113b, a second measurement result display area 113c, a normalized value display area 113d, a first judgment result display area 113e, a second judgment result display area 113f, and a comprehensive judgment result display area 113g. The graph 113a displays a graph showing the relationship between a value related to the expression level of the cancer marker gene and a first threshold value and between a normalized value obtained by normalizing a value related to the expression level of the cancer marker gene, on the basis of the expression level of the housekeeping gene and a second threshold value, in the measurement sample displayed in the measurement sample information display 112. In FIG. 7, the graph 113a shows the relationship between the value related to the expression level of the cancer marker gene and the first threshold value on the abscissa and the relationship between the normalized value and the second threshold value on the ordinate. The first measurement result display area 113b displays the value related to the expression level of the cancer marker gene. In FIG. 7, the first measurement result display area 113b displays the amount of CEA m-RNA (copies/µL) as the value related to the expression level of the cancer marker gene. The second measurement result display area 113c displays the value related to the expression level of the housekeeping gene. In FIG. 7, the second measurement result display area 113c displays the amount of β-actin m-RNA (copies/µL) as the value related to the expression level of the housekeeping gene. The normalized value display area 113d displays the normalized value. In FIG. 7, 113d displays, as the normalized value, a value obtained by dividing the amount of CEA m-RNA by the amount of β-actin m-RNA. The first judgment result display area 113e displays information on a judgment result (first judgment result) concerning the presence or absence of cancer cells in the measurement sample, on the basis of the result of comparison between the value related to the expression level of the cancer marker gene and the first threshold value. In FIG. 7, the first judgment result display area 113e displays "−" as information on the first judgment result. "−" indicates that cancer cells are not present in the measurement sample. The second judgment result display area 113f displays information on a judgment result (second judgment result) concerning the presence or absence of cancer cells in the measurement sample, on the basis of the result of comparison between the normalized value and the second threshold value. In FIG. 7, the second judgment result display area 113f displays "+" as information on the second judgment result. "+" indicates that cancer cells are present in the measurement sample. The comprehensive judgment result display area 113g displays information on a comprehensive judgment result concerning the presence or absence of cancer cells in the measurement sample, on the basis of the first and second judgment results. In FIG. 7, the comprehensive judgment result display area 113g displays "+" as information on the comprehensive judgment result.

EXAMPLES

Hereinafter, the present invention is described in more detail by reference to the Examples, but the present invention is not limited to the following examples.

(1) Collection of Abdominal Cavity Washes and Preparation of Samples

In operation of 50 patients with stomach cancer, abdominal cavity washes were collected for examination of stomach cancer metastasis. Specifically, the abdominal cavity was opened, then 100 mL physiological saline was injected into the abdominal cavity (subhepatic, left subdiaphragmatic and/or Douglas pouch sites) to wash the cavity, and the wash was recovered. The recovered abdominal cavity wash was centrifuged at about 3,000×g for 10 minutes, and then the supernatant was removed, whereby about 50 to 100 μL sample was obtained.

These 50 patients consisted of 17 patients recognized to have stomach cancer metastasis and 33 patients not recognized to have metastasis by cell biopsy.

(2) RT-PCR

The sample prepared in (1) was treated by using RNeasy Mini Kit (manufactured by QIAGEN) according to manufacture's instructions, to give 50 μL of a purified RNA solution.

The resulting purified RNA solution was measured for the amount of CEA mRNA as a cancer marker gene and the amount of β-actin mRNA as a housekeeping gene respectively by quantitative RT-PCR (TaqMan™ RT-PCR) with the following primers in a reaction solution having the composition shown below.

Primers for amplification of CEA mRNA:

```
Forward primer:              (SEQ ID NO: 1)
5'-agacaatcacagtctctgcgga-3'

Reverse primer:              (SEQ ID NO: 2)
5'-atccttgtcctccacgggtt-3'

TaqMan probe:                (SEQ ID NO: 17)
5'-FAM-agctgcccaagccct-TAMRA-3'
```

Primers for amplification of β-actin mRNA:

```
Forward primer:              (SEQ ID NO: 13)
5'-ccacactgtgcccatctacg-3'

Reverse primer:              (SEQ ID NO: 14)
5'-aggatcttcatgaggtagtcagtcag-3'

TaqMan probe:                (SEQ ID NO: 18)
5'-FAM-atgccctcccccatgccatcctgcgt-TAMRA-3'
```

Composition for RT-PCR reaction solution 1×one-step TaqMan™ RT-PCR Master mix (manufactured by Applied Biosystems)
Forward primer: 300 nM
Reverse primer: 300 nM
TaqMan probe: 250 nM
Purified RNA solution: 1 μL
Total: 25 μL Using PRISM7700 (manufactured by Applied Biosystems), the reaction solution was subjected to reverse transcription at 50° C. for 30 minutes and at 95° C. for 15 minutes to amplify cDNA, then subjected to 40 cycles of PCR reaction each cycle consisting of PCR reaction at 95° C. for 30 seconds and at 72° C. for 30 seconds, and measured for its fluorescence intensity.

A standard curve wherein the concentrations of mRNA were plotted against fluorescence intensity was previously prepared by using standard solutions containing known amounts of mRNA prepared by in vitro transcription of each gene cloned from cultured cells, and the amounts of CEA mRNA and β-actin mRNA in the sample were determined on the basis of the standard curve. The unit is the number of copies of mRNA/μL.

The determined amount of CEA mRNA is shown in "CEA Absolute Value" in Table 2. This value was compared with a threshold value (first threshold vale) of 20 copies/μL. Samples having the mRNA in an amount equal to or higher than the threshold value were judged as positive "+", while samples having the mRNA in an amount lower than the threshold value were judged as negative "−". The judgment result is shown in "Absolute Value Judgment" in Table 3.

A value (normalized value) obtained by dividing the determined amount of CEA mRNA by the amount of β-actin mRNA. The normalized value thus obtained is shown in "CEA/Actin Normalized Value" in Table 2. This value was compared with a threshold value (second threshold value) of $1 \times 10^{-5}$. Samples having a normalized value equal to or higher than the threshold value were judged as positive "+", while samples having a normalized value lower than the threshold value were judged as negative "−". The judgment result is shown in "Normalized Value Judgment" in Table 3.

Samples that were positive in the absolute value judgment and/or the normalized value judgment were judged to be positive "+" for the presence of cancer cells. This result is shown in "Comprehensive Judgment" in Table 3.

Figure 8:
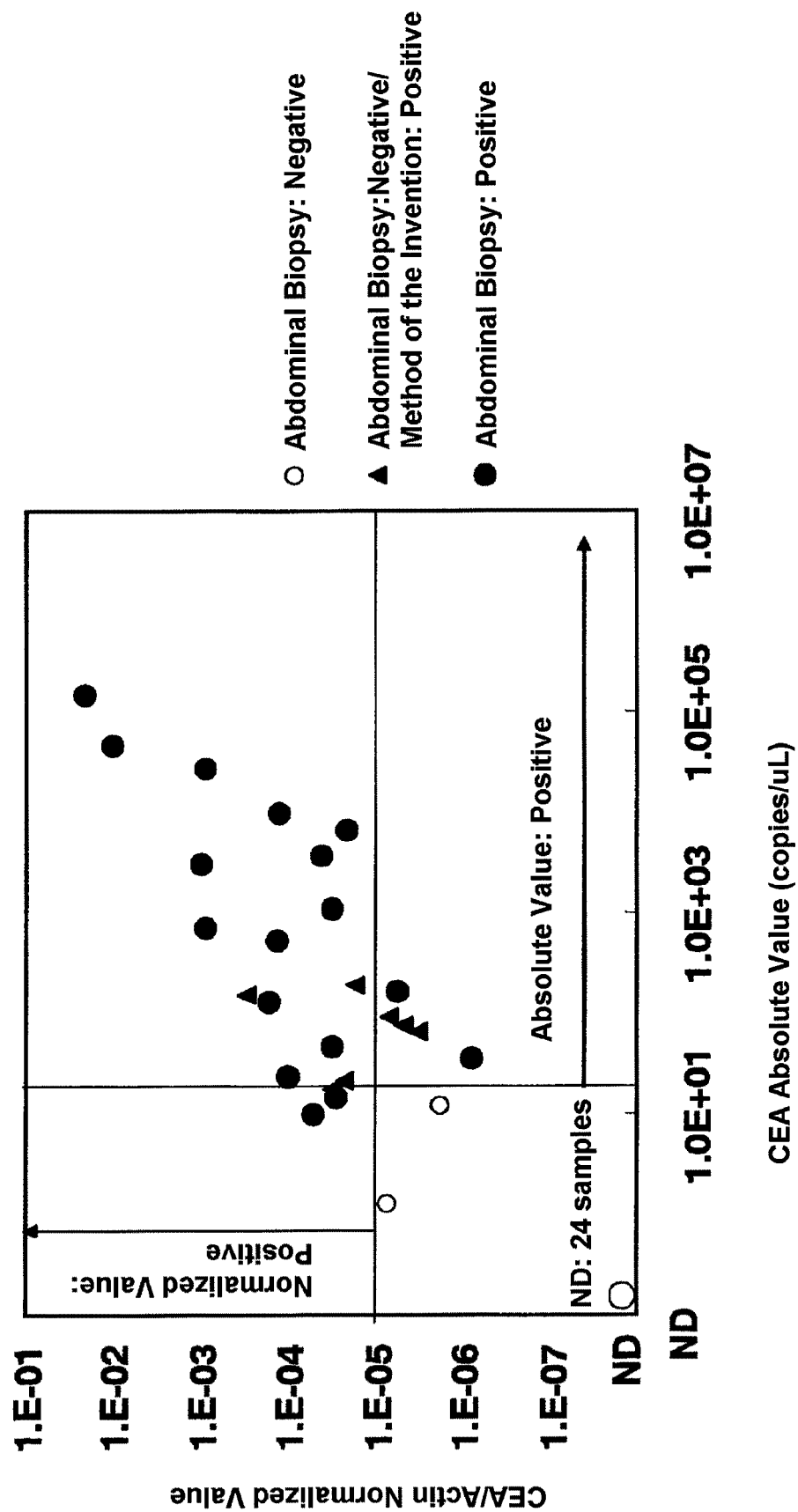
FIG. 8 is a graph showing results in the Examples.

The results in Table 2 and 3 are shown in the graph in FIG. 8 wherein "CEA Absolute Value" is shown on the abscissa and "CEA/Actin Normalized Value on the ordinate.

TABLE 2

| No. | Site | Biopsy Result | CEA Absolute Value | Actin Absolute Value | CEA/Actin Normalized Value |
|---|---|---|---|---|---|
| 1 | left subdiaphragmatic | + | 1.5E+01 | 5.0E+05 | 2.9E−05 |
| 2 | Douglas pouch | + | 7.1E+02 | 8.1E+05 | 8.8E−04 |
| 3 | left subdiaphragmatic | + | 1.3E+02 | 7.6E+05 | 1.7E−04 |
| 4 | Douglas pouch | + | 5.2E+02 | 3.9E+06 | 1.3E−04 |
| 5 | Douglas pouch | + | 4.7E+04 | 4.5E+06 | 1.0E−02 |
| 6 | Douglas pouch | + | 3.7E+03 | 8.9E+07 | 4.1E−05 |
| 7 | subhepatic | + | 1.7E+02 | 3.0E+07 | 5.6E−06 |
| 8 | subhepatic | + | 2.4E+01 | 2.4E+05 | 9.9E−05 |
| 9 | subhepatic | + | 3.0E+03 | 3.0E+06 | 1.0E−03 |
| 10 | left subdiaphragmatic | + | 4.7E+01 | 1.5E+06 | 3.2E−05 |
| 11 | Douglas pouch | + | 2.7E+04 | 3.1E+07 | 8.9E−04 |
| 12 | Douglas pouch | + | 1.5E+05 | 7.0E+06 | 2.2E−02 |
| 13 | left subdiaphragmatic | + | 1.0E+01 | 1.9E+05 | 5.2E−05 |
| 14 | Douglas pouch | + | 6.5E+03 | 3.1E+08 | 2.1E−05 |
| 15 | Douglas pouch | + | 9.6E+03 | 7.6E+07 | 1.3E−04 |
| 16 | Douglas pouch | + | 1.1E+03 | 3.6E+07 | 3.1E−05 |
| 17 | Douglas pouch | ± | 2.9E+01 | 3.6E+07 | 7.9E−07 |
| 18 | Douglas pouch | − | ND | 8.9E+05 | — |
| 19 | left | − | ND | 8.1E+05 | — |
| 20 | left subdiaphragmatic | − | 7.7E+01 | 1.6E+07 | 4.7E−06 |
| 21 | subhepatic | − | 1.8E+01 | 5.7E+05 | 3.1E−05 |
| 22 | Douglas pouch | − | ND | 1.2E+05 | — |
| 23 | left subdiaphragmatic | − | ND | 9.2E+05 | — |
| 24 | Douglas pouch | − | ND | 5.8E+05 | — |
| 25 | Douglas pouch | − | ND | 9.7E+07 | — |
| 26 | left subdiaphragmatic | − | ND | 1.7E+07 | — |
| 27 | Douglas pouch | − | ND | 3.7E+07 | — |
| 28 | Douglas pouch | − | 1.9E+02 | 1.1E+07 | 1.7E−05 |
| 29 | Douglas pouch | − | ND | 7.4E+05 | — |
| 30 | Douglas pouch | − | ND | 2.2E+06 | — |
| 31 | Douglas pouch | − | 6.7E+01 | 2.1E+07 | 3.3E−06 |
| 32 | Douglas pouch | − | ND | 7.5E+06 | — |
| 33 | Douglas pouch | − | 1.3E+00 | 1.8E+05 | 7.4E−06 |
| 34 | left | − | ND | 2.5E+05 | — |
| 35 | left subdiaphragmatic | − | 9.4E+01 | 1.4E+07 | 6.9E−06 |
| 36 | Douglas pouch | − | ND | 4.8E+06 | — |
| 37 | Douglas pouch | − | ND | 1.2E+08 | — |
| 38 | Douglas pouch | − | ND | 6.0E+05 | — |
| 39 | Douglas pouch | − | ND | 1.0E+07 | — |
| 40 | Douglas pouch | − | ND | 5.1E+07 | — |
| 41 | Douglas pouch | − | ND | 5.3E+05 | — |
| 42 | Douglas pouch | − | ND | 5.3E+05 | — |
| 43 | Douglas pouch | − | ND | 6.5E+06 | — |

TABLE 2-continued

| No. | Site | Biopsy Result | CEA Absolute Value | Actin Absolute Value | CEA/Actin Normalized Value |
|---|---|---|---|---|---|
| 44 | Douglas pouch | − | ND | 2.3E+06 | — |
| 45 | Douglas pouch | − | ND | 2.6E+06 | — |
| 46 | left subdiaphragmatic | − | ND | 4.5E+06 | — |
| 47 | left subdiaphragmatic | − | ND | 1.5E+05 | — |
| 48 | Douglas pouch | − | 1.1E+01 | 4.9E+06 | 2.3E−06 |
| 49 | left subdiaphragmatic | − | 2.8E+00 | 2.2E+05 | 1.2E−05 |
| 50 | left subdiaphragmatic | − | 1.1E+02 | 3.8E+07 | 2.8E−06 |

TABLE 3

| No. | Absolute Value Judgment | Normalized Value Judgment | Comprehensive Judgment | Note |
|---|---|---|---|---|
| 1 | − | + | + | |
| 2 | + | + | + | |
| 3 | + | + | + | |
| 4 | + | + | + | |
| 5 | + | + | + | |
| 6 | + | + | + | |
| 7 | + | − | + | |
| 8 | + | + | + | |
| 9 | + | + | + | |
| 10 | + | + | + | |
| 11 | + | + | + | |
| 12 | + | + | + | |
| 13 | − | + | + | |
| 14 | + | + | + | |
| 15 | + | + | + | |
| 16 | + | + | + | |
| 17 | + | − | + | |
| 18 | − | − | − | |
| 19 | − | − | − | |
| 20 | + | − | + | peritoneal recurrence |
| 21 | − | + | + | Douglas pouch: positive |
| 22 | − | − | − | |
| 23 | − | − | − | |
| 24 | − | − | − | |
| 25 | − | − | − | |
| 26 | − | − | − | |
| 27 | − | − | − | |
| 28 | + | + | + | progression in gastric wall: high |
| 29 | − | − | − | |
| 30 | − | − | − | |
| 31 | + | − | + | |
| 32 | − | − | − | |
| 33 | − | − | − | |
| 34 | − | − | − | |
| 35 | + | − | + | Douglas pouch: positive |
| 36 | − | − | − | |
| 37 | − | − | − | |
| 38 | − | − | − | |
| 39 | − | − | − | |
| 40 | − | − | − | |
| 41 | − | − | − | |
| 42 | − | − | − | |
| 43 | − | − | − | |
| 44 | − | − | − | |
| 45 | − | − | − | |
| 46 | − | − | − | |
| 47 | − | − | − | |
| 48 | − | − | − | |
| 49 | − | + | + | peritoneal recurrence |
| 50 | + | − | + | Douglas pouch: positive |

From the results in Table 2 and 3, the samples Nos. 20, 21, 28, 31, 35, 49 and 50 among samples judged by biopsy to be negative for the presence of cancer cells were judged to have cancer cells by the method of the present invention. Among these samples, the 6 samples except for the sample No. 31 were samples judged to be positive for the presence of cancer cells, in another abdominal cavity wash collected from a site other than the abdominal cavity wash used as the sample, or were samples from patients who showed high stomach cancer progression in the gastric wall or had peritoneal recurrence. That is, it can be appreciated that the method of the present invention can be used to detect a very small amount of cancer cells even in samples judged by biopsy to be free from cancer cells, that is, in samples judged to be negative for stomach cancer metastasis, thus enabling more accurate judgment of the presence or absence of cancer cells and consequently enabling providing information useful for judgment of stomach cancer metastasis.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is;

1. A method for determining a presence of a cancer cell in a sample obtained from a patient, comprising:
   obtaining a sample suspected of containing a cancer cell from a patient;
   obtaining a value related to an expression level of a cancer marker gene and a value related to an expression level of a housekeeping gene;
   a first comparing step of comparing the value related to the expression level of the cancer marker gene with a first threshold value, wherein the first threshold value is a value equal to or less than a value related to an expression level of the cancer marker gene in a sample containing cancer cells and a value higher than a value related to an expression level of the cancer marker gene in a sample free of cancer cells;
   a normalizing step of normalizing the value related to the expression level of the cancer marker gene based on the value related to the expression level of the housekeeping gene;
   a second comparing step of comparing the normalized value obtained from the normalizing step with a second threshold value, wherein the second threshold value is a value equal to or less than a normalized value obtained by normalizing the value of the expression level of the cancer marker gene in the sample containing cancer cells based on the value related to the expression level of the housekeeping gene and a value higher than a normalized value obtained by normalizing the value of the expression level of the cancer marker gene in the sample free of cancer cells; and
   judging the cancer cell is present in the sample based on the result of the comparison of the first comparing step and the result of the second comparing step.

2. The method according to claim 1, wherein the judging step is performed so as to judge that the cancer cell exists in the sample, when the value related to the expression level of the cancer marker gene is not less than the first threshold value and/or when the normalized value is not less than the second threshold value.

3. The method according to claim 1, wherein the judging step comprises:
   a first judging step of judging whether the cancer cell exists or not in the sample based on a comparison result of the first comparing step; and
   a second judging step of judging whether the cancer cell exists or not in the sample based on a comparison result of the second comparing step.

4. The method according to claim 3, wherein the first judging step is performed so as to judge that the cancer cell exists in the sample, when the value related to the expression level of the cancer marker gene is not less than the first threshold value.

5. The method according to claim 3, wherein the second judging step is performed so as to judge that the cancer cell exists in the sample, when the normalized value is not less than the second threshold value.

6. The method according claim 3, wherein the judging step is performed so as to judge that the cancer cell exists in the sample when at least one selected from the first judging step and the second judging step judges that the cancer cell exists in the sample.

7. The method according to claim 1, wherein the cell obtained from a patient is a cell included in a lymph node tissue, blood or a body cavity wash.

8. The method according to claim 1, wherein the value related to the expression level of the cancer marker gene is a value obtained by measuring an amplification product derived from a nucleic acid amplification using mRNA of the cancer marker gene as a template, and the value related to the expression level of the housekeeping gene is a value obtained by measuring an amplification product derived from a nucleic acid amplification using mRNA of the housekeeping gene as a template.

9. The method according to claim 1, wherein the cancer marker gene is a gene of cytokeratin, carcinoembryonic antigen, MUC1 mucin or mammaglobin.

10. The method according to claim 1, wherein the housekeeping gene is a gene of glyceraldehyde-3-phosphate dehydrogenase, cyclophilin, β-actin or α-tubulin.

11. A method for determining a presence of a cancer cell in a sample obtained from a patient, comprising:

obtaining a sample suspected of containing a cancer cell from a patient;

obtaining a value related to an expression level of a cancer marker gene and a value related to an expression level of a housekeeping gene;

a first comparing step of comparing the value related to the expression level of the cancer marker gene with a first threshold value, wherein the first threshold value is a value equal to or less than a value related to an expression level of the cancer marker gene in a sample containing cancer cells and a value higher than a value related to an expression level of the cancer marker gene in a sample free of cancer cells;

a normalizing step of normalizing the value related to the expression level of the cancer marker gene based on the value related to the expression level of the housekeeping gene, when the value related to the expression level of the cancer marker gene is less than the first threshold value in the first comparing step;

a second comparing step of comparing the normalized value obtained from the normalizing step with a second threshold value, wherein the second threshold value is a value equal to or less than a normalized value obtained by normalizing the value of the expression level of the cancer marker gene in the sample containing cancer cells based on the value related to the expression level of the housekeeping gene and a value higher than a normalized value obtained by normalizing the value of the expression level of the cancer marker gene in the sample free of cancer cells; and judging the cancer cell is present in the sample based on a comparison result of the first comparing step or the second comparing step.

12. The method according to claim 11, wherein the cell obtained from a patient is a cell contained in a lymph node tissue, blood or a body cavity wash.

13. The method according to claim 11, wherein the value related to the expression level of the cancer marker gene is a value obtained by measuring an amplification product derived from a nucleic acid amplification using mRNA of the cancer marker gene as a template, and the value related to the expression level of the housekeeping gene is a value obtained by measuring an amplification product derived from a nucleic acid amplification using mRNA of the housekeeping gene as a template.

14. The method according to claim 11, wherein the cancer marker gene is a gene of cytokeratin, carcinoembryonic antigen, MUC1 mucin or mammaglobin.

15. The method according to claim 11, wherein the housekeeping gene is a gene of glcyeraldehyde-3-phosphate dehydrogenase, cyclophilin, β-actin or α-tubulin.

16. A method for determining a presence of a cancer cell in a sample obtained from a patient, comprising:

obtaining a sample suspected of containing a cancer cell from a patient;

obtaining a value related to an expression level of a cancer marker gene and a value related to an expression level of a housekeeping gene;

a first comparing step of comparing the value related to the expression level of the cancer marker gene with a first threshold value, wherein the value related to the expression level of the cancer marker gene is not normalized;

a normalizing step of normalizing the value related to the expression level of the cancer marker gene based on the value related to the expression level of the housekeeping gene;

a second comparing step of comparing the normalized value obtained from the normalizing step with a second threshold value; and judging the cancer cell is present in the sample based on the result of the comparison of the first comparing step and the result of the second comparing step.

* * * * *